US009360462B2

(12) United States Patent
Taneda et al.

(10) Patent No.: US 9,360,462 B2
(45) Date of Patent: Jun. 7, 2016

(54) GAS CHROMATOGRAPH MASS SPECTROMETER

(71) Applicant: SHIMADZU CORPORATION, Kyoto-shi, Kyoto (JP)

(72) Inventors: Katsuyuki Taneda, Kyoto (JP); Shuichi Kawana, Kyoto (JP)

(73) Assignee: SHIMADZU CORPORATION, Tokyo (JP)

( * ) Notice: Subject to any disclaimer, the term of this patent is extended or adjusted under 35 U.S.C. 154(b) by 459 days.

(21) Appl. No.: 13/661,395

(22) Filed: Oct. 26, 2012

(65) Prior Publication Data

US 2014/0116111 A1    May 1, 2014

(51) Int. Cl.
*G01N 30/18* (2006.01)
*G01N 30/10* (2006.01)
*G01N 30/72* (2006.01)
*G01N 30/12* (2006.01)

(52) U.S. Cl.
CPC .............. *G01N 30/18* (2013.01); *G01N 30/10* (2013.01); *G01N 30/7206* (2013.01); *G01N 2030/126* (2013.01)

(58) Field of Classification Search
CPC ........................... G01N 30/18; G01N 30/7206
USPC ........................................................ 73/23.37
See application file for complete search history.

(56) References Cited

U.S. PATENT DOCUMENTS

| | | | | |
|---|---|---|---|---|
| 4,008,388 A * | 2/1977 | McLafferty | ........... | G06F 19/703 250/281 |
| 7,148,475 B2 * | 12/2006 | Cozic | ................. | G01N 30/7213 250/281 |
| 2005/0080578 A1 * | 4/2005 | Klee | .................... | H01J 49/0009 702/85 |
| 2006/0097148 A1 * | 5/2006 | Cozic | ................. | G01N 30/7213 250/288 |
| 2007/0084302 A1 * | 4/2007 | Tsuchihashi | ........... | G01N 30/24 73/864.11 |
| 2010/0077838 A1 * | 4/2010 | McCauley | ............. | G01N 30/32 72/23.42 |
| 2011/0100093 A1 * | 5/2011 | Kawana | ................. | G01N 30/28 73/23.42 |

FOREIGN PATENT DOCUMENTS

| | | |
|---|---|---|
| JP | 10-48190 A | 2/1998 |
| JP | 11-101788 A | 4/1999 |

(Continued)

OTHER PUBLICATIONS

Translation of JP 10048190.*

(Continued)

*Primary Examiner* — Peter Macchiarolo
*Assistant Examiner* — Nathaniel Kolb
(74) *Attorney, Agent, or Firm* — Sughrue Mion, PLLC

(57) ABSTRACT

A gas chromatograph mass spectrometer including: an oven for gas chromatography, a mass spectrometry part, a sample vaporization chamber, a gas supply part, and a control part. When the replacement operation of a septum or a glass insert begins, the control part controls the gas supply part so that the flow rate of a carrier gas has a constant pressure and then controls heaters so that temperature is equal to or less than a temperature at which replacement is possible. When temperature becomes equal to or less than the temperature at which replacement is possible and the replacement operation of the septum or the glass insert is completed, the control part controls the heaters so that the temperature is an analysis temperature and controls the gas supply part to employ the same control method for the flow rate of the carrier gas as that before the replacement operation is begun.

7 Claims, 5 Drawing Sheets

(56) References Cited

FOREIGN PATENT DOCUMENTS

| | | | |
|---|---|---|---|
| JP | 2000-304751 | A | 11/2000 |
| JP | 2001-208737 | A | 8/2001 |
| JP | 2005-345452 | A | 12/2005 |
| JP | 2011-242175 | A | 12/2011 |

OTHER PUBLICATIONS

Notification of Reasons for Rejection dated Aug. 6, 2013 in Japanese Patent Application 2010-112557.
Notification of Reasons for Rejection dated Jan. 21, 2014 in Japanese Patent Application 2010-112557.

* cited by examiner

GAS CHROMATOGRAPH MASS SPECTROMETER

TECHNICAL FIELD

The present invention relates to a gas chromatograph mass spectrometer equipped with a sample vaporization chamber having a septum or a glass insert.

BACKGROUND ART

In recent years, gas chromatograph mass spectrometers (hereafter called "GC/MSs") combining a gas chromatograph part (hereafter called a "GC part"), a mass spectrometry part (hereafter called an "MS" part), and a control part for controlling the GC part and the MS part have been widely used in the qualitative or quantitative analyses of various samples.

FIG. 5 is a schematic block diagram showing an example of a conventional GC/MS. A GC/MS 101 is provided with a GC part 10, an MS part 50, an interface part 70 disposed between the GC part 10 and the MS part 50, and a control part 160.

The control part 160, which is realized by a personal computer, is provided with a CPU 161 and a memory 162, and an input device 63 having a keyboard, a mouse, or the like and a display device 64 for displaying setting content or analysis results are further connected to the control part 160. The operations of the GC part 10, the MS part 50, and the interface part 70 are generally controlled by such a control part 160 based on setting content inputted by the input device 63.

When the CPU 161 is described in terms of blocks of the functions processed by the CPU 161, the CPU 161 has a temperature control part 161a for controlling a first heater 24, a second heater 38 (see FIG. 2), a third heater 72, or the like, a flow rate control part 161b for controlling a flow rate control unit (gas supplying part) 40, and an analysis control part 61c for receiving an ion intensity signal from a detector 55.

The GC part 10 is provided with an oven 20 for gas chromatography, a sample vaporization chamber 30 into which a sample is introduced, and a flow rate control unit (gas supplying part) 40 for supplying a carrier gas.

The oven 20 for gas chromatography is provided with a cubic housing 21 enclosed by four walls on the top, bottom, left, and right, a back wall, and a front door serving as a front wall, and a tubular column 22 through which a sample gas passes, a first heater 24 for heating the housing 21, and a temperature sensor 25 for detecting a temperature T are housed inside the housing 21.

In such an oven 20 for gas chromatography, when an operator inputs a temperature $T_1'$ (for example, 200° C.) at the time of analysis using the input device 63, the temperature control part 161a of the CPU 161 stores the analysis temperature $T_1'$ in the memory 162 and sets the inside of the housing 21 to the analysis temperature $T_1'$ by supplying power to the first heater 24 based on the analysis temperature $T_1'$ stored in the memory 162 and the temperature T detected by the temperature sensor 25.

As a result, with the oven 20 for gas chromatography, if a sample gas is introduced into the inlet end of the gas column 22, the respective components in the sample gas are separated while the gas passes through the inside of the column 22 at the analysis temperature $T_1'$, and the respective separated components sequentially reach the outlet end of the column 22 thereafter.

The interface part 70 is provided with a tubular casing 71 and a third heater 72 for heating the casing 71. The outlet end of the column 22 is inserted into the casing 71 so as to extend to an ionization chamber 52 of the MS part 50.

With such an interface part 70, it is possible to maintain the temperature of the outlet end of the column 22 at approximately the same temperature as the analysis temperature $T_1'$ inside the oven 20 for gas chromatography, and as a result, it is possible to ensure that the flow of the sample gas is not stagnated by the interface part 70.

The MS part 50 is provided with a parallelepiped-shaped vacuum chamber 51, a vacuum pump 56 for creating a vacuum inside the vacuum chamber 51, and a sample source 58 for adjustment in which PFTBA (perfluorotributylamine) or the like for assessing whether oxygen is present inside the column 22 is sealed. An ionization chamber 52, an ion lens 53, a quadrupole mass filter 54 serving as a mass separator, and a detector 55 for obtaining an ion intensity signal are sequentially disposed inside the vacuum chamber 51 along the advancing direction of ions, and an ion gauge (ionization vacuum gauge) 57 for detecting the pressure (degree of vacuum) $P_{MS}$ of the vacuum chamber 51 is also disposed.

With such an MS part 50, sample molecules are ionized by the ionization chamber 52, and the generated ions are drawn to the outside of the ionization chamber 52. The drawn ions are converged by the ion lens 53 and introduced into the quadrupole mass filter 54. A voltage determined by overlaying a direct current voltage and a high-frequency voltage is applied to the quadrupole mass filter 54 by a power supply circuit (not shown), and only ions having a mass (specifically, a mass-charge-ratio) corresponding to the applied voltage pass through the space of the quadrupole mass filter 54 in the major axis direction and reach the detector 55. At this time, if the voltage applied to the quadrupole mass filter 54 is gradually changed, for example, the mass of the ions which may pass through the quadrupole mass filter 54 also changes, so a mass spectrum demonstrating the relationship between mass and ion intensity is obtained by detecting the size of the current corresponding to the number of ions reaching the detector 55 while gradually changing the voltage applied to the quadrupole mass filter 54 with the analysis control part 61c.

Next, the sample vaporization chamber 30 and the flow rate control unit 40 of the GC part 10 will be described (for example, see Patent Document 1). FIG. 2 is a magnified cross-sectional view of the sample vaporization chamber 30 and the flow rate control unit 40.

The sample vaporization chamber 30 is provided with a tubular metal casing 31 and a second heater 38 for heating the outer peripheral surface of the casing 31.

The casing 31 can be divided into an upper casing 31b and a lower casing 31a, and separating the casing makes it possible to dispose a tubular glass insert 37a made of glass inside.

The upper casing 31b has a sample introduction port 32 which is formed on the top surface and through which a liquid sample S is introduced.

The lower casing 31a has a carrier gas introduction port 33 which is formed on the left side wall and through which a carrier gas is introduced, a purging port 34 which is formed on the right side wall and through which the carrier gas is discharged, a column connection port 35 which is formed on the bottom surface and is connected to the inlet side of the column 22, and a split port 36 which is formed on the right side wall and through which part of the sample gas infused into the casing 31 is discharged together with the carrier gas.

A roughly columnar silicon rubber septum 32a is disposed on the sample introduction port 32, and the septum 32a is fixed to the upper casing 31b as it is pressed downward by a septum nut 32b. With this septum 32a, the operator can drip the liquid sample S into the casing 31 at the time of analysis by thrusting a needle 91 of a micro-syringe 90 containing the liquid sample S into the septum 32a. Since the septum 32a has elasticity, the hole which opens when the needle 91 is inserted into the septum 32a immediately closes when the needle 91 is removed.

The glass insert 37a is supported and disposed by a circular sealing ring 37b inside the lower casing 31a. With such a glass insert 37a, the operator can vaporize the liquid sample S as it passes through the space inside the glass insert 37a from the upper side to the lower side at the time of analysis by disposing the needle 91 of the micro-syringe 90 in the upper part of the internal space formed in the glass insert 37a.

The upper casing 31b is fixed to the lower casing 31a as it is pressed downward by the sealing nut 37c.

The column connection port 35 is connected to the inlet end of the column 22 and is fixed by a column nut 35a.

The carrier gas is sealed in a carrier gas supply source 41. One end of a gas introduction tube 42 is connected to the carrier gas supply source 41, and the other end of the gas introduction tube 42 is connected to the carrier gas introduction port 33 via a gas flow rate adjustment valve 43. The flow rate control unit 40 for supplying the carrier gas is formed by the gas introduction tube 42, the gas flow rate adjustment valve 43, and the carrier gas supply source 41.

One end of a gas discharge tube 46 is connected to the split port 36, and a gas flow rate adjustment valve 47 is further connected to the gas discharge tube 46. As a result, when the gas flow rate adjustment valve 47 is open, a certain proportion of the carrier gas is discharged through the split port 36.

One end of a gas discharge tube 44 is connected to the purging port 34, and a pressure sensor 45 for detecting the pressure P of the inside of the casing 31 is further disposed on the gas discharge tube 44.

In such a sample vaporization chamber 30 and a flow rate control unit 40, the operator inputs a setting so that the flow rate of the carrier gas is a "constant linear velocity" using the input device 63 at the time of analysis. As a result, the flow rate control part 161b of the CPU 161 stores "constant linear velocity" in the memory 162 and controls the gas flow rate adjustment valve 43 so that the flow rate is the "constant linear velocity" stored in the memory 162, which causes the carrier gas to be supplied to the upper part of the casing 31 through the gas introduction tube 42, and further controls the gas flow rate adjustment valve 47 so that a prescribed amount of the carrier gas is fed to the column 22 and a prescribed amount of the carrier gas is fed to the split port 36.

At this time, the casing 31 is heated by the second heater 38 to a temperature equal to or higher than the vaporization temperature of the liquid sample S, and when the liquid sample S is infused into space inside the glass insert 37a, the liquid sample S is immediately vaporized in the space inside the glass insert 37a so that it is sent to the inlet end of the column 22 at a "constant linear velocity" along with the carrier gas flow.

Here, a "constant linear velocity" means that the rate is controlled so that the volume of the carrier gas passing through the cross-sectional area of the column 22 per unit time is constant.

Incidentally, since the glass insert 37a disposed inside the casing 31 of the sample vaporization chamber 30 makes direct contact with the sample S, it is prone to contamination by the adherence of the vaporization residue or the like of the sample S. As a result, when the glass insert 37a becomes contaminated, it is necessary to replace the old glass insert 37a with a new glass insert 37a.

Here, the replacement operation for replacing the glass insert 37a will be described. FIG. 3 is an exploded view of the sample vaporization chamber 30.

First, when air is immixed inside the column 22 at a temperature equal to or less than the high analysis temperature $T_1$', the stationary phase film inside the column 22 is oxidized, and as a result, the lifespan of the column 22 is reduced, so the operator inputs a replacement temperature $T_2$' (for example, 20° C.) with the input device 63 so as to reduce the temperature T of the sample vaporization chamber 30 or the column 22 to a temperature in the vicinity of room temperature.

At this time, if the temperature T of the column 22 becomes a temperature in the vicinity of the replacement temperature $T_2$' while the flow rate of the carrier gas is set to a "constant linear velocity," it may not be possible to control the carrier gas with the pressure required to keep the linear velocity constant depending on the length or inside diameter of the column 22, which may cause the flow rate control part 161b of the CPU 161 to generate an error signal. Therefore, before inputting the replacement temperature $T_2$', the operator uses the input device 63 to input a setting so that the flow rate of the carrier gas has a "constant pressure" or to input a pressure that can be controlled at the replacement temperature $T_2$'.

Here, a "constant pressure" means that the pressure is controlled so that the pressure PGC detected by the pressure sensor 45 is constant.

Next, after the operator confirms that the temperature T of the sample vaporization chamber 30 or the column 22 has become a temperature in the vicinity of the replacement temperature $T_2$' while viewing the display device 64, the operator loosens and removes the sealing nut 37c from the lower casing 31a and extracts the glass insert 37a from the lower casing 31a. Next, the operator inserts the new glass insert 37a into the lower casing 31a and tightens the sealing nut 37c onto the lower casing 31a.

Finally, the operator uses the input device 63 to input the analysis temperature T1' so as to increase the temperature T of the sample vaporization chamber 30 or the column 22 to the analysis temperature $T_1$' and to further input a setting so that the flow rate of the carrier gas is a "constant linear velocity" or to input the pressure before the change to the replacement temperature $T_2$'.

In addition, if the elasticity of the septum 32a deteriorates due to long-term use or the number of locations with holes increases as the number of uses increases, the holes will not be completely closed, and as a result, the carrier gas will leak to the outside from the inside of the casing 31. When performing analysis under such conditions with a gas leak, there may be a deviation in the retention time, which is the time required for a peak to occur in a chromatogram, or the peak area may be reduced, which may inhibit accurate analysis, so it is necessary to perform a replacement operation for replacing the septum 32a.

Such an operation for replacing the septum 32a is also executed by the operator with the same procedure as that of the replacement operation for replacing the glass insert 37a.

PRIOR ART DOCUMENTS

Patent Document 1—Japanese Unexamined Patent Application Publication H11-101788

SUMMARY OF THE INVENTION

However, in a replacement operation such as that described above, an inexperienced operator may start the step for loosening and removing the sealing nut 37c from the lower casing 31a before the temperature T of the sample vaporization chamber 30 or the column 22 drops to the vicinity of room temperature, and as a result, the operator may endure a burn injury, or air may be immixed inside the high-temperature column 22, which may reduce the lifespan of the column 22.

In addition, before the temperature T of the sample vaporization chamber 30 or the column 22 drops to the vicinity of room temperature, it is necessary to input a setting so that the flow rate of the carrier gas has a "constant pressure" or to input an appropriate pressure which can be controlled at the stage when the temperature drops, but there are cases in which the temperature T of the sample vaporization chamber 30 or the column 22 drops to the vicinity of room temperature without any input from the operator, and as a result, the CPU 161, being unable to control the pressure, generates an error signal.

Further, it is also necessary for the operator to introduce PFTBA into the MS part 50 and to remove the air penetrating the inside of the sample vaporization chamber 30 or the column 22 while confirming the amount of oxygen present inside the column 22, before bringing the temperature T of the sample vaporization chamber 30 or the column 22 to the to the analysis temperature $T_1'$.

That is, in order to perform the replacement operation for replacing the septum 32a or the glass insert 37a of the sample vaporization chamber 30, it is necessary to execute various steps with a predetermined procedure, which is an extremely difficult operation for an inexperienced operator.

Therefore, the purpose of the present invention is to provide a gas chromatograph mass spectrometer with which the septum or glass insert of a sample vaporization chamber can be easily and accurately replaced by anyone.

The gas chromatograph mass spectrometer of the present invention, which was conceived in order to solve the problems described above, is a gas chromatograph mass spectrometer equipped with: an oven for gas chromatography provided with a housing, a column disposed inside the housing, and a first heater for heating the housing; a sample vaporization chamber provided with a casing having a sample introduction port through which a liquid sample is introduced, a carrier gas introduction port through which a carrier gas is introduced, and a column connection port connected to the inlet end of the column and a second heater for heating the casing; a mass spectrometry part which is connected to the outlet end of the column and has a detector for detecting an ion intensity signal of the liquid sample; a gas supplying part for supplying a carrier gas to the carrier gas introduction port of the sample vaporization chamber; and a control part having an input device for inputting setting content including an analysis temperature; wherein a septum into which the needle of a syringe containing a liquid sample is inserted is disposed in the sample introduction port, a glass insert is disposed for vaporizing the liquid sample inside said casing, and the control part obtains an ion intensity signal from the detector while controlling the first heater, the second heater, and the gas supplying part based on the setting content inputted by the input part; and wherein when the replacement operation of the septum or glass insert is begun, the control part controls the gas supplying part so that the flow rate of the carrier gas has a constant pressure and controls the heaters so that the temperature is equal to or less than a temperature at which replacement is possible; and when the temperature becomes equal to or less than the temperature at which replacement is possible and the replacement operation of the septum or glass insert is completed, the control part controls the heaters so that the temperature becomes an analysis temperature and then controls the gas supplying part to employ the same control method for the flow rate of the carrier gas as that before the replacement operation is begun.

Here, the "temperature at which replacement is possible," which is an arbitrary temperature predetermined by the designer or the like, is the upper limit temperature at which the stationary phase film inside the column does not oxidize even when oxygen is present inside the column, such as 30° C., for example.

With the gas chromatograph mass spectrometer of the present invention, when the replacement operation of the septum or the glass insert is begun, the control part controls the gas supplying part so that the flow rate of the carrier gas has a "constant pressure" and then controls the heaters so that the temperature is equal to or less than the temperature at which replacement is possible. That is, it is unnecessary for the operator to input a setting so that the flow rate of the carrier gas has a "constant pressure" or input an appropriate value so that the pressure of the carrier gas can be controlled even if the temperature T of the column 22 becomes the "temperature at which replacement is possible," and it is also unnecessary for the operator to input the replacement temperature $T_2'$.

When the temperature then becomes equal to or less than the temperature at which replacement is possible and the replacement operation of the septum or the glass insert is completed, the control part controls the heaters so that the temperature becomes the analysis temperature $T_1'$ and controls the gas supplying part so that the control method for the flow rate of the carrier gas is the same as that before the replacement operation is begun—for example, so that the flow rate of the carrier gas is a "constant linear velocity." Here, if the gas supplying part is controlled so that the flow rate of the carrier gas has a "constant pressure" before the replacement operation is begun, the gas supplying part will be controlled so that the flow rate of the carrier gas has a "constant pressure." That is, it is unnecessary for the operator to input the analysis temperature $T_1'$ or to return the pressure or flow rate of the carrier gas to the value prior to the beginning of the replacement operation.

As described above, with the gas chromatograph mass spectrometer of the present invention, the septum or the glass insert of the sample vaporization chamber can be replaced easily and accurately by anyone.

In addition, the gas chromatograph mass spectrometer of the present invention may be configured so that the control method for the flow rate of the carrier gas before the replacement operation is begun controls the gas supplying part so that the flow rate of the carrier gas is a constant linear velocity.

Moreover, the gas chromatograph mass spectrometer of the present invention may be configured so that the mass spectrometry part is provided with an ionization vacuum gauge for measuring the degree of vacuum of the mass spectrometry part; the control part assesses whether to generate an error signal based on a signal from the ionization vacuum gauge; when the replacement operation of the septum or glass insert is begun, the control part controls the gas supplying part so that the flow rate of the carrier gas is 0 and administers control so that the power of the ionization vacuum gauge is turned OFF; and when the replacement operation of the septum or glass insert is completed, the control part controls the gas supplying part to employ the same control method for the flow rate of the carrier gas as that before the replacement operation is begun and administers control so that the power of the ionization vacuum gauge is turned ON.

At the time of the replacement of the septum or the glass insert, air infiltrates the vacuum chamber through the column, and the control part is notified of the deterioration of the degree of vacuum indicated by the ionization vacuum meter, but with the gas chromatograph mass spectrometer of the present invention, the notification of the deterioration of the degree of vacuum indicated by the ionization vacuum meter can be prevented by turning the power of the ionization vacuum system OFF. As a result, the control part assesses that it is dangerous during the replacement operation, which makes it possible to stop the operation of the entire gas chromatograph mass spectrometer of the present invention.

In addition, the gas chromatograph mass spectrometer of the present invention may be configured so that when the replacement operation of the septum or glass insert is completed, the control part obtains an ion intensity signal from the detector, calculates the intensity of the mass spectrum of nitrogen based on the ion intensity signal, and assesses whether to control the heaters so that the temperature is the analysis temperature.

With the gas chromatograph mass spectrometer of the present invention, it is possible to expel air infiltrating the inside of the sample vaporization chamber or the column before the temperature of the vaporization chamber or the column becomes the analysis temperature $T_1'$.

The gas chromatograph mass spectrometer of the present invention may also be configured so that the control part assesses that the replacement operation of the septum or glass insert has begun based on a replacement operation start signal inputted by the input device; and assesses that the replacement operation of the septum or glass insert has been completed based on a replacement operation completion signal inputted by the input device.

Further, the gas chromatograph mass spectrometer of the present invention may configured so that the control part controls the heaters so that the temperature is equal to or less than the temperature at which replacement is possible and then displays a screen indicating that the temperature has become equal to or less than the temperature at which replacement is possible on a display device.

DETAILED DESCRIPTION OF THE EXEMPLARY EMBODIMENTS

Embodiments of the invention will be described below using the drawings. The present invention is not limited to the embodiments described below, and it goes without saying that various modes are included within a scope that does not deviate from the gist of the present invention.

Figure 1:
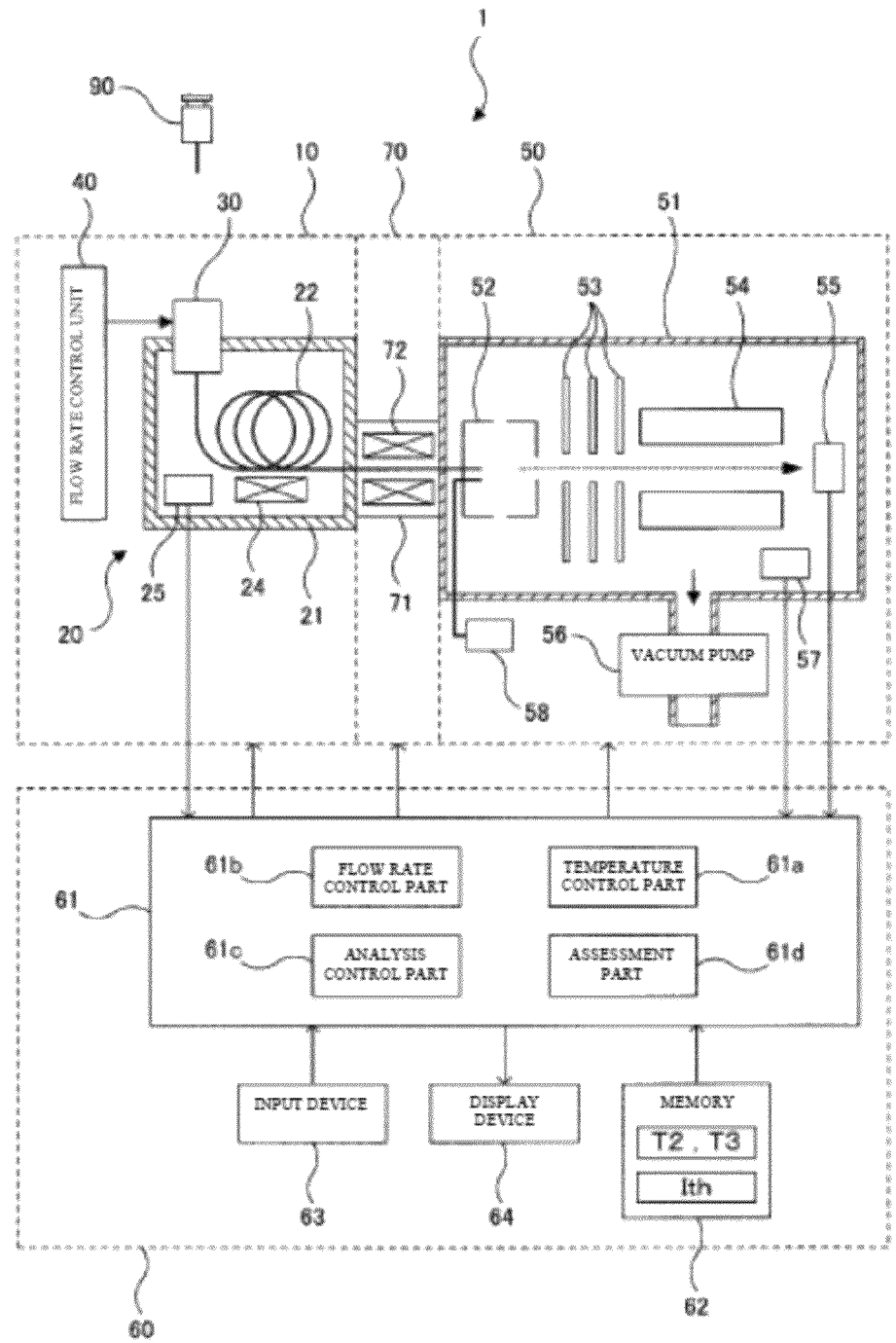
FIG. 1 is a schematic block diagram showing an example of the GC/MS of the present invention.

FIG. 1 is a schematic block diagram showing an example of the GC/MS of the present invention. Components which are the same as those of the conventional GC/MS 101 described above are labeled with the same symbols.

A GC/MS 1 is provided with a GC part 10, an MS part 50, an interface part 70 disposed between the GC part 10 and the MS part 50, and a control part 60.

The control part 60, which is realized by a personal computer, is provided with a CPU 61 and a memory 62, and an input device 63 having a keyboard, a mouse, or the like and a display device 64 for displaying setting content or analysis results are further connected to the control part 60.

Figure 2:
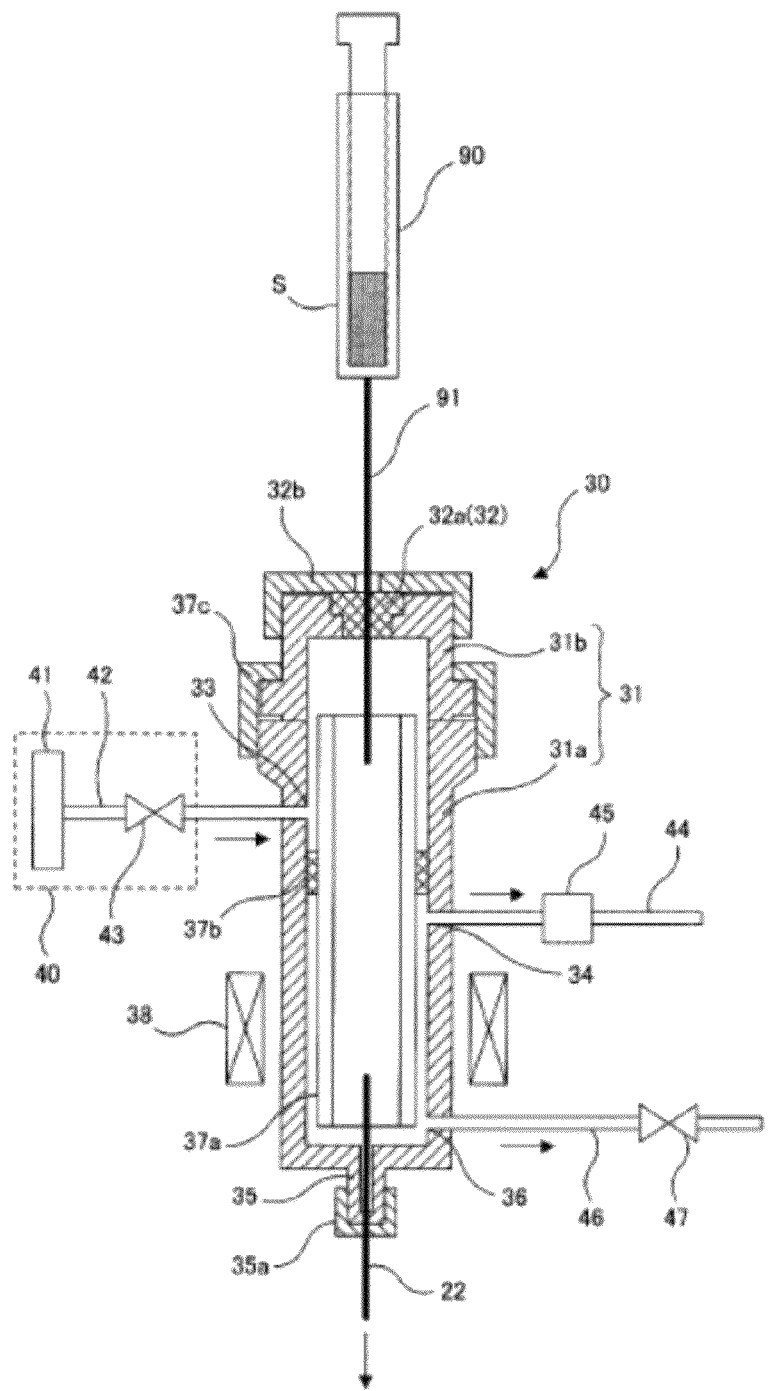
FIG. 2 is a magnified cross-sectional view of the sample vaporization chamber and the flow rate control unit.
Figure 3:
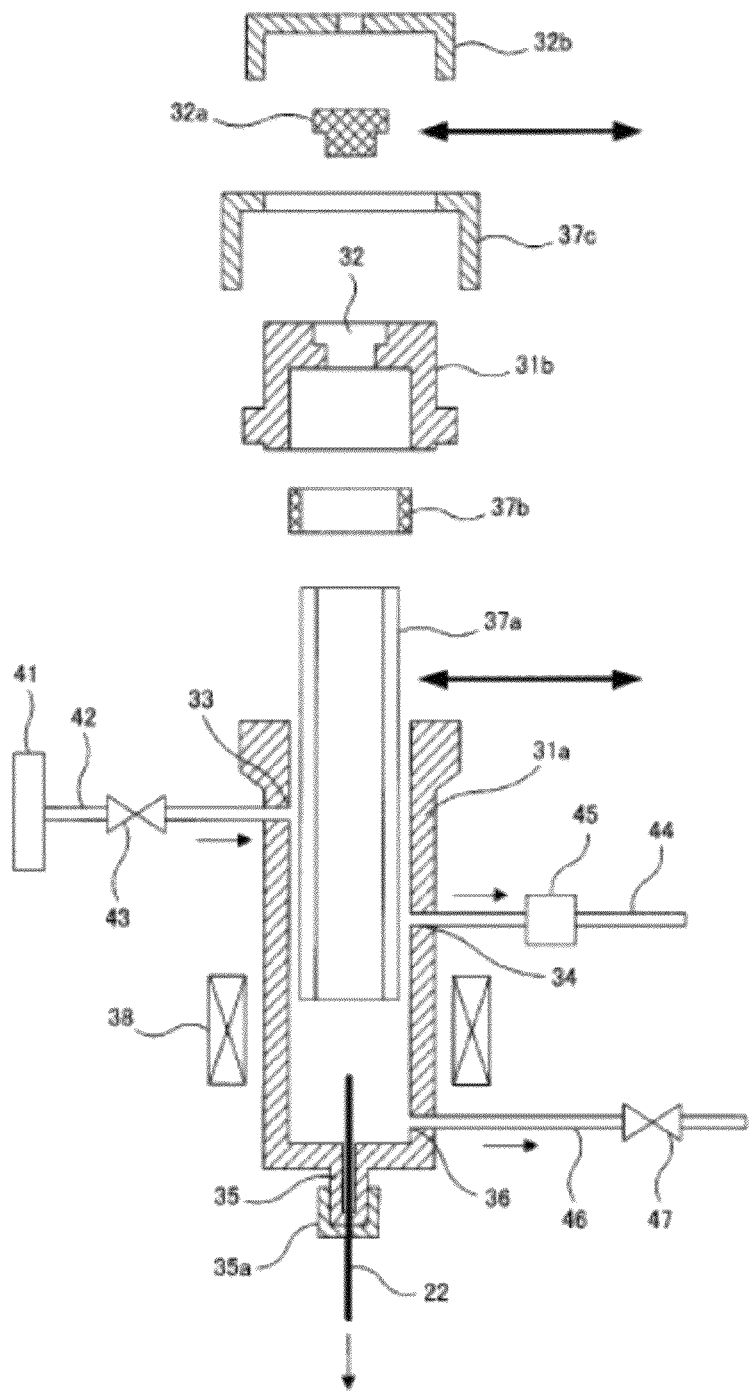
FIG. 3 is an exploded view of the vaporization chamber.

When the CPU 61 is described in terms of blocks of the functions processed by the CPU 61, the CPU 61 has a temperature control part 61a for controlling a first heater 24, a second heater 38 (see FIG. 2), a third heater 72, or the like, a flow rate control part 61b for controlling a flow rate control unit (gas supplying part) 40, an analysis control part 61c for receiving an ion intensity signal from a detector 55, and an assessment part 61d for assessing whether air is present inside the column 22.

In addition, a temperature $T_2$ at which replacement is possible (for example, 30° C.) is stored in advance in the memory 62 as the upper limit temperature at which the stationary phase film inside the column 22 will not be oxidized even if oxygen is present inside the column 22, and a set temperature $T_3$ (for example, 20° C.) is stored in advance as a target temperature for reducing the temperature of the column 22 to a temperature equal to or less than the temperature $T_2$ at which replacement is possible in the GC/MS 1.

Further, a threshold $I_{th}$ for assessing whether a prescribed amount of oxygen is present inside the column 22 is stored in advance in the memory 62.

When the operator inputs a setting so that the flow rate of the carrier gas is a "constant linear velocity" using the input device 63, the flow rate control part 61b stores "constant linear velocity" in the memory 62 and controls a gas flow rate adjustment valve 43 so that the flow rate is the "constant linear velocity" stored in the memory 62, which causes the carrier gas to be supplied to the upper part of a casing 31 through a gas introduction tube 42, and further controls a gas flow rate adjustment valve 47 so that a prescribed amount of the carrier gas is fed to the column 22 and a prescribed amount of the carrier gas is fed to a split port 36.

Similarly, when the operator inputs a setting so that the flow rate of the carrier gas has a "constant pressure" using the input device 63, the flow rate control part 61b stores "constant pressure" in the memory 62 and controls the gas flow rate adjustment valve 43 so that the pressure P detected by a pressure sensor 45 is constant. The setting may be controlled to be either a "constant linear velocity" or a "constant pressure" before the replacement operation is begun.

In addition, when the operator inputs "start replacement operation" using the input device 63, the flow rate control part 61b of the present invention stores "start replacement operation" in the memory 62, and the gas flow rate adjustment valves 43 and 47 are controlled so that the flow rate of the carrier gas has a "constant pressure" based on the "start replacement operation" stored in the memory 62.

Furthermore, when the operator inputs "start replacement operation" using the input device 63, the flow rate control part 61b of the present invention stores "end replacement operation" in the memory 62, and after the temperature control part 61a sets the temperature to the analysis temperature $T_1'$ based on the "end replacement operation" stored in the memory 62, the gas flow rate adjustment valves 43 and 47 are controlled so that the control method for the flow rate of the carrier gas is the same as that before the replacement operation is begun—for example, so that the flow rate of the carrier gas is a "constant linear velocity."

When the operator inputs the analysis temperature $T_1'$ using the input device 63, the temperature control part 61a stores the analysis temperature $T_1'$ in the memory 62 and controls the temperature to the analysis temperature $T_1'$ by heating by means of supplying power to a first heater 24, a second heater 38, and a third heater 72 based on the analysis temperature $T_1'$ stored in the memory 62 and the temperature T detected by sensors such as the temperature sensor 25.

In addition, when the operator inputs "start replacement operation" using the input device 63, the temperature control part 61a of the present invention stores "start replacement operation" in the memory 62, and after the flow rate control part 61b sets the flow rate so as to have a "constant pressure" based on the "start replacement operation" stored in the memory 62 and then stops the supply of power to the first heater 24, the second heater 38, and the third heater 72 so as to set the temperature to the set temperature T3. When the temperature T detected by the temperature sensor 25 becomes a temperature equal to or less than the temperature T2 at which replacement is possible, "replacement operation possible" is displayed on the display device 64.

Further, when the operator inputs "end replacement operation" using the input device 63, the temperature control part 61a of the present invention stores "end replacement operation" in the memory 62 and supplies power to the first heater 24, the second heater 38, and the third heater 72 based on the "end replacement operation" stored in the memory 62 and a signal from the assessment part 61d so as to set the temperature to the analysis temperature $T_1'$.

The analysis control part 61c administers control to store the ion intensity signal obtained by the detector 55 in the memory 62, to execute various types of operation processing based on the ion intensity signal, and to display the analysis results on the display device 64.

For example, a mass spectrum is created by assigning the intensity of ions when a mass scan is performed at a given retention time to the vertical axis and assigning the mass-to-charge ratio (m/z) to the horizontal axis. At this time, multiple mass spectra corresponding to each of the components successively eluted from the column are obtained by intermittently and repeatedly performing mass scans at certain intervals.

As a result, after multiple such mass spectra are obtained, a mass chromatogram or the like of ions of a selected mass-to-charge ratio can be obtained by focusing on a given m/z and expanding and drawing the intensity of ions in the time axis direction.

When the replacement operation of the septum 32a or the glass insert 37a is completed, the assessment part 61d obtains an ion intensity signal from the detector 55 by introducing PFTBA into the MS part 50, calculates the intensity ratio of the mass spectrum of nitrogen with respect to the intensity of the mass spectrum of PFTBA based on the ion intensity signal, and then controls the first heater 24, the second heater 38, and the third heater 72 so that the temperature is the analysis temperature $T_1'$.

Specifically, the intensity ratio of the peak of nitrogen ions (mass 28) with respect to the intensity of the peak of PFTBA ions (mass 69) is calculated based on the mass spectra obtained by the analysis control part 61c, and when the intensity ratio is equal to or greater than the threshold $I_{th}$, it is assessed that there is a prescribed amount of oxygen inside the column 22—that is, the first heater 24, the second heater 38, and the third heater 72 are continually controlled so that the temperature is the set temperature T3. On the other hand, when the intensity ratio is less than the threshold $I_{th}$, it is assessed that there is not a prescribed amount of oxygen inside the column 22—that is a signal is outputted to the temperature control part 61a so as to control the first heater 24, the second heater 38, and the third heater 72 so that the temperature is the analysis temperature $T_1'$.

Figure 4:
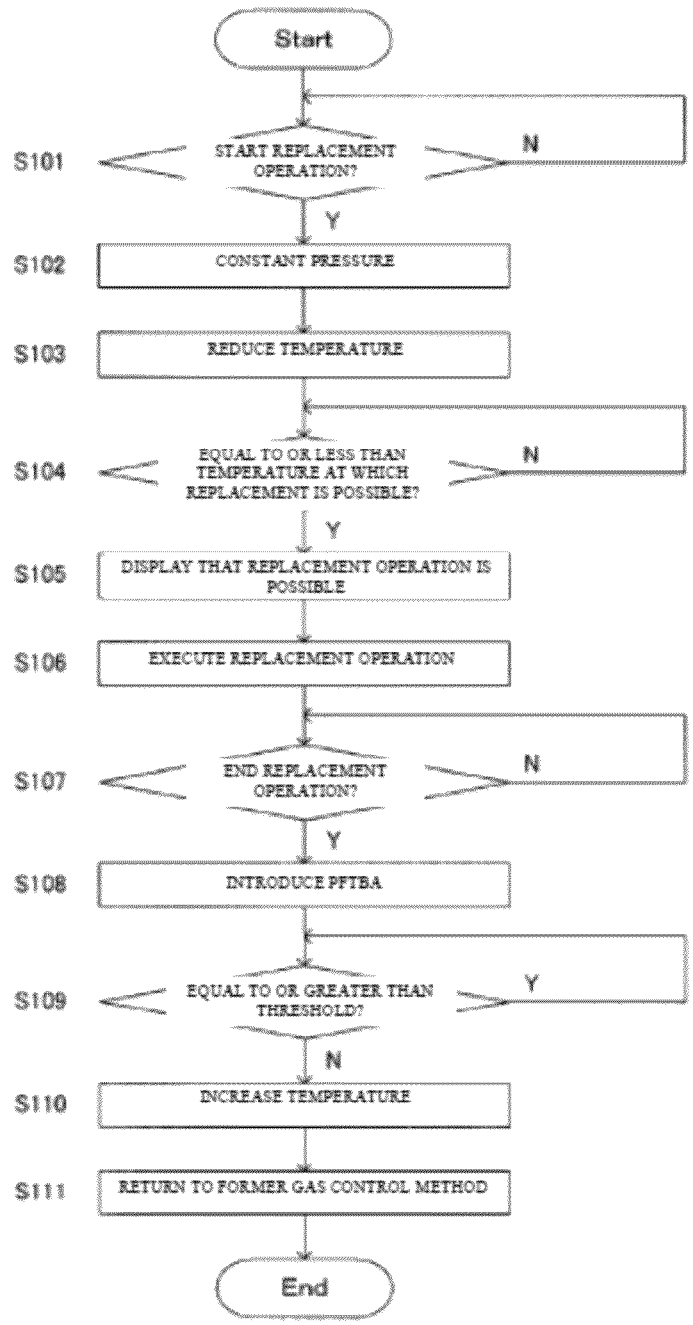
FIG. 4 is a flowchart showing the procedure of the replacement operation.
Figure 5:
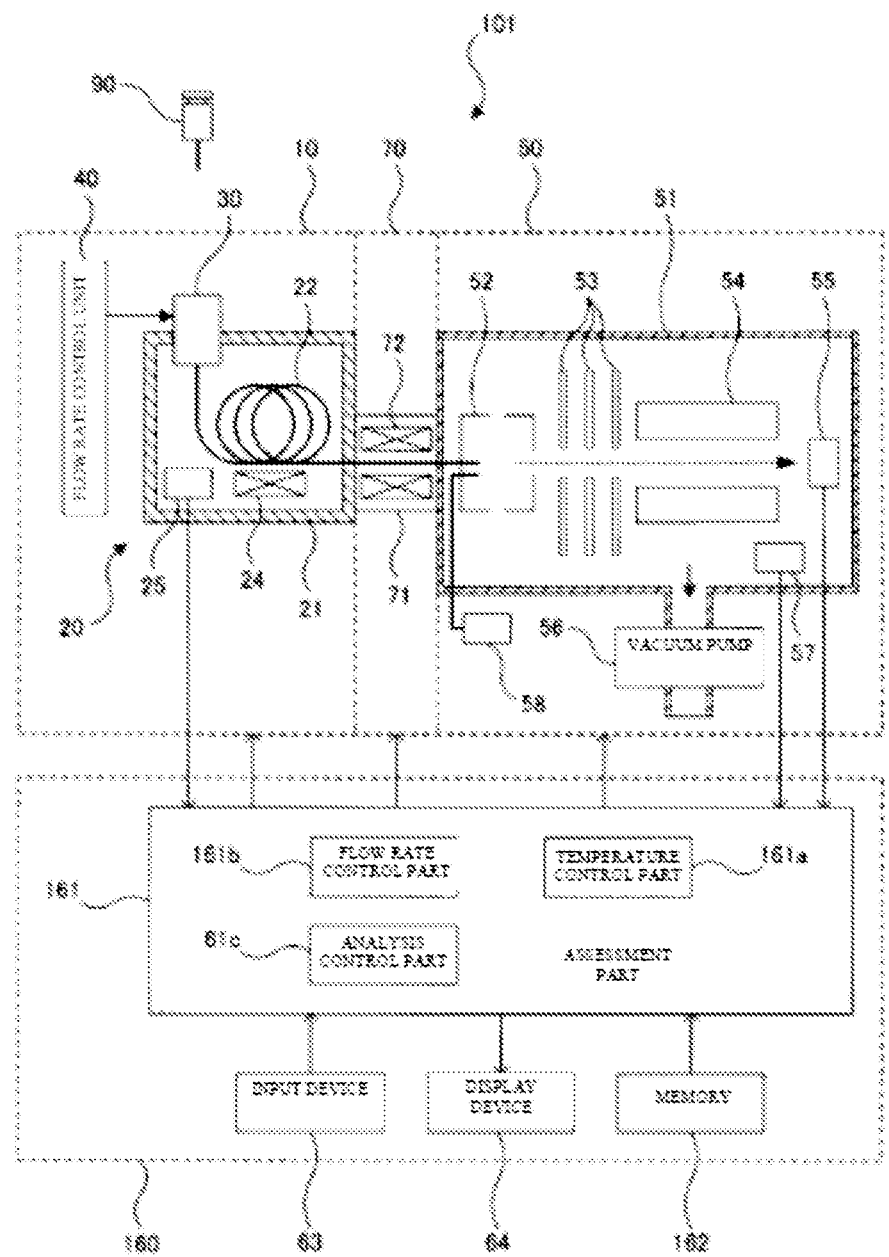
FIG. 5 is a schematic block diagram showing an example of a conventional GC/MS.

Next, the replacement method for replacing the glass insert 37a will be described. FIG. 4 is a flowchart showing the procedure of the replacement method.

First, in the processing of step S101, the flow rate control part 61b assesses whether "start replacement operation" has been inputted by the operator. If it is assessed that "start replacement operation" has not been inputted, the processing of step S101 is repeated.

On the other hand, if it is assessed that "start replacement operation" has been inputted, the flow rate control part 61b controls the gas flow rate adjustment valves 43 and 47 so that the flow rate of the carrier gas has a "constant pressure" in the processing of step S102.

Next, in the processing of step S103, the temperature control part 61a sets the temperature to the set temperature $T_3$ by stopping the supply of power to the first heater 24, the second heater 38, and the third heater 72.

Next, in the processing of step S104, the temperature control part 61a assesses whether the temperature has become a temperature equal to or less than the temperature T2 at which replacement is possible. If it is assessed that the temperature is not equal to or less than the temperature $T_2$ at which replacement is possible, the processing of step S104 is repeated.

On the other hand, when it is assessed that the temperature is equal to or less than the temperature $T_2$ at which replacement is possible, "replacement operation possible" is displayed on the display device 64 in the processing of step S105. As a result, the operator recognizes that the glass insert 37a may be replaced.

Next, in the processing of step S106, the operator replaces the glass insert 37a.

Next, in the processing of step S107, the assessment part 61d assesses whether "end replacement operation" has been inputted. If it is assessed that "end replacement operation" has not been inputted, the processing of step S107 is repeated.

On the other hand, when it is assessed that "end replacement operation" has been inputted, in the processing of step S108, the assessment part 61d obtains an ion intensity signal from the detection part 55 by introducing PFTBA into the MS part 50 and calculates the intensity ratio of the peak of nitrogen ions (mass 28) with respect to the intensity of the peak of PFTBA ions (mass 69) based on the ion intensity signal.

Next, in the processing of step S109, the assessment part 61d assesses whether the intensity ratio is equal to or greater than the threshold $I_{th}$. If it is assessed that the intensity ratio is equal to or greater than the threshold $I_{th}$, the processing of step S109 is repeated.

On the other hand, when it is assessed that the intensity ratio is less than the threshold Ith, the temperature control part 61a sets the temperature to the analysis temperature $T_1'$ by supplying power to the first heater 24, the second heater 38, and the third heater 72 in the processing of step S110.

Next, in the processing of step S111, the flow rate control part 61b controls the gas flow rate adjustment valves 43 and 47 so that the control method for the flow rate of the carrier gas is the same as before the replacement operation is begun—for example, so that the flow rate of the carrier gas is a "constant linear velocity."

As described above, with the gas chromatograph mass spectrometer 1 of the present invention, the septum 32a or the glass insert 37a of the sample vaporization chamber 30 can be easily and accurately replaced by anyone.

(1) In the gas chromatograph mass spectrometer 1 of the present invention, the flow rate control part 61b may also be configured so as to control the gas flow rate adjustment valves 43 and 47 so that the flow rate of the carrier gas has a "constant pressure" when the operator inputs "start replacement operation" using the input device 63, and the control part may be configured so as to control the gas flow rate adjustment valves so that the flow rate of the carrier gas becomes 0 and to administer control so that the power supply of the ion gauge is turned OFF when the operator inputs "start replacement operation" using the input device. When the operator then inputs "end replacement operation" using the input device, the control part controls the gas flow rate adjustment valves so that the control method for the flow rate of the carrier gas is the same as that before the replacement operation is begun—for example, so that the flow rate of the carrier gas is a "constant linear velocity"—and administers control so that the power supply of the ion gauge is turned ON.

(2) The gas chromatograph mass spectrometer 1 of the present invention was configured so that the operator inputs "start replacement operation" using the input device 63, but the device may also be configured so that a measuring instrument 45 sets "start replacement operation" by detecting changes in the pressure PGC inside the casing 31.

The present invention can be used for a gas chromatograph mass spectrometer.

EXPLANATION OF SYMBOLS

20: oven for gas chromatography
21: housing
22: column
24, 38, 72: heaters
31: casing
32: sample introduction port
32a: septum
33: carrier gas introduction port
35: column connection port
37a: glass insert
40: flow rate control unit (gas supplying part)
50: mass spectrometry part (MS part)
55: detector
60: control part
63: input device
90: syringe
91: needle

What is claimed is:

1. A method of replacing a septum or glass insert of a gas chromatograph mass spectrometer, the gas chromatograph mass spectrometer comprising:
an oven for gas chromatography provided with a housing, a column disposed inside said housing, and a first heater for heating said housing;
a sample vaporization chamber provided with a casing having a sample introduction port through which a liquid sample is introduced, a carrier gas introduction port through which a carrier gas is introduced, and a column connection port connected to the inlet end of said column and a second heater for heating said casing;
a mass spectrometry part which is connected to the outlet end of said column and has a detector for detecting an ion intensity signal of said liquid sample;
a gas supplying part for supplying a carrier gas to the carrier gas introduction port of said sample vaporization chamber; and
a control part having an input device for inputting setting content including an analysis temperature;
wherein said septum into which the needle of a syringe containing a liquid sample is inserted is disposed in said sample introduction port, said glass insert is disposed for vaporizing the liquid sample inside said casing, and said control part obtains an ion intensity signal from said detector while controlling the first heater, the second heater, and the gas supplying part based on the setting content inputted by said input part;
the method comprising:
receiving an input signal to said input device corresponding to starting a replacement operation for replacement of said septum or glass insert;
in response to said input signal, said control part controls the gas supplying part so that the flow rate of said carrier gas has a constant pressure and controls the heaters so that the temperature is equal to or less than a temperature at which replacement is possible; and
when the temperature becomes equal to or less than the temperature at which replacement is possible and the replacement operation of said septum or glass insert is completed, said control part obtains an ion intensity signal from said detector, calculates the intensity of the mass spectrum of nitrogen based on the ion intensity signal and based on the intensity of the mass spectrum of nitrogen determines to control the heaters so that the temperature becomes an analysis temperature, and then controls the gas supplying part to employ the same control method for the flow rate of said carrier gas as that before the replacement operation is begun
wherein said control part calculates an intensity ratio of the mass spectrum of a first ion with respect to a mass spectrum of a second ion, and determines to control the heaters so that the temperature becomes an analysis temperature when the intensity ratio is less than a threshold corresponding to a state in which there is not a prescribed amount of oxygen inside said column.

2. The method according to claim 1, wherein said control method for the flow rate of the carrier gas before the replacement operation is begun controls the gas supplying part so that the flow rate of said carrier gas is a constant linear velocity.

3. The method according to claim 1, wherein:
said mass spectrometry part is provided with an ionization vacuum gauge for measuring the degree of vacuum of said mass spectrometry part;
said control part assesses whether to generate an error signal based on a signal from said ionization vacuum gauge;
when the replacement operation of said septum or glass insert is begun, said control part controls the gas supplying part so that the flow rate of said carrier gas is 0 and administers control so that the power of said ionization vacuum gauge is turned OFF; and
when the replacement operation of said septum or glass insert is completed, said control part controls the gas supplying part to employ the same control method for the flow rate of the carrier gas as that before the replacement operation is begun and administers control so that the power of said ionization vacuum gauge is turned ON.

4. The method according to claim 1, wherein:
said control part assesses that the replacement operation of said septum or glass insert has begun based on a replacement operation start signal inputted by said input device; and
assesses that the replacement operation of said septum or glass insert has been completed based on a replacement operation completion signal inputted by said input device.

5. The method according to claim 1, wherein said control part controls the heaters so that the temperature is equal to or less than the temperature at which replacement is possible and then displays a screen indicating that the temperature has become equal to or less than the temperature at which replacement is possible on a display device.

6. The method according to claim 1, wherein
before said input signal to said input device corresponding to starting a replacement operation, the control method for the flow rate of the carrier gas is a constant linear velocity, and when the temperature becomes equal to or less than the temperature at which replacement is possible and the replacement operation of said septum or glass insert is completed, said control part obtains the ion intensity signal from said detector, calculates the intensity of the mass spectrum of nitrogen based on the ion intensity signal and based on the intensity of the mass spectrum of nitrogen determines to control the heaters so that the temperature becomes the analysis temperature, and then controls the gas supplying part to revert to the control method for the flow rate of the carrier gas which is the constant linear velocity.

7. The method according to claim 1, wherein the first ion is nitrogen and the second ion is PFTBA (perfluorotributylamine).

* * * * *